United States Patent [19]

Mukai et al.

[11] 4,203,933

[45] May 20, 1980

[54] METHOD OF PURIFYING TRIARYL PHOSPHATE

[76] Inventors: Sadayoshi Mukai; Yoshiaki Otani; Osamu Yamaguchi, all c/o Nissin Electric Co., Ltd., 47, Umezu Takase-cho, Ukyo-ku, Kyoto, Japan

[21] Appl. No.: 904,261

[22] Filed: May 9, 1978

[30] Foreign Application Priority Data

May 20, 1977 [JP] Japan .................................. 52-59229

[51] Int. Cl.² .............................................. C07F 9/09
[52] U.S. Cl. .................................... 260/990; 260/966
[58] Field of Search ......................................... 260/990

[56] References Cited

U.S. PATENT DOCUMENTS

| | | | |
|---|---|---|---|
| 1,462,306 | 7/1923 | St. John | 260/990 |
| 1,840,335 | 1/1932 | ter Horst | 260/990 |
| 2,605,279 | 7/1952 | Edwards et al. | 260/990 |

OTHER PUBLICATIONS

Grin, "Clay Mineralogy," McGraw-Hill, 1962, pp. 320–321 & 326–331.
Siddiqui, "Bleaching Earths," Pergamon Press, 1968, pp. 1–3, 44–45 & 50–55.
Kirk-Othmer, "Encyclopedia of Chemical Technology" vol. 5, (1964), pp. 541–555.

*Primary Examiner*—Anton H. Sutto
*Attorney, Agent, or Firm*—Christensen, O'Connor, Johnson & Kindness

[57] ABSTRACT

A method of purifying triaryl phosphate to be used as electrical insulating oil, comprising a first step of washing the phosphate with the aqueous solution of alkali, a second step of diluting the phosphate with aromatic insulating oil, a third step of treating the diluted phosphate with acid clay in an atmosphere of dry gas so that the acid clay adsorbs the impurities in the phosphate and a fourth step of treating the phosphate under reduced pressure for removal of any remaining impurities therefrom.

26 Claims, No Drawings

METHOD OF PURIFYING TRIARYL PHOSPHATE

This invention relates to a method of purifying triaryl phosphate to be used as insulating oil in electrical devices such as capacitors.

As compared with the conventional mineral oil that has been in wide use as insulating oil, triaryl phosphate (to be referred to simply as the phosphate hereinafter) has a higher dielectric constant and is incombustible so that at present it has come to be widely used as insulating oil in various kinds of electrical devices, particularly in electrical capacitors in place of mineral oil.

Although the phosphate has the above-mentioned good characteristics, it is inferior to mineral oil with respect to dielectric loss tangent and volume resistivity. There has therefore been a strong demand for improvement of these characteristics of the phosphate.

It has been considered as the chief reason for the above-mentioned inferior characteristics of the phosphate that the reaction of esterifcation of the phosphate produces monoaryl phosphate, diaryl phosphate, chlorinated monoaryl phosphate, hydrogen chloride, etc. which together with water remain as impurities in the triaryl phosphate produced.

Generally, an adsorbent is used to remove water from oil. As such adsorbent acid clay and activated clay are well known and widely used. For use either clay is first dried at 100° C. to 200° C. for about 5 hours and 1% to 5% by weight of the clay is mixed with the phosphate and the mixture is stirred for about 1 hour so that the clay adsorbs water in the phosphate, after which the adsorbent is removed from the phosphate.

Various kinds of triayl phosphates have been treated in the above manner, but the treated phosphates have not attained characteristics good enough to enable them practically usable as insulating oil. The reason for this is considered to be that by the prior art adsorbing treatment alone it is impossible to remove from the phosphate the previously mentioned impurities produced in the process of esterification of the phosphate.

Accordingly, the primary object of the invention is to provide a method of purifying triaryl phosphate so as to improve its electrical characteristics.

Another object of the invention is to provide such a method as aforesaid by which the phosphate can be purified to such an extent that the impurities produced therein in the esterification process are substantially removed from the phosphate.

In a preferred embodiment of the invention, the purifying method comprises: a first step of washing triaryl phosphate containing impurities with an aqueous solution of an alkali compound; a second step of diluting the phosphate with aromatic insulating oil; a third step of adsorbing the impurities with acid clay in an atmosphere of a dry gas; and a fourth step of removing remaining impurities from the phosphate under reduced pressure.

The first step is intended to neutralize the impurities produced in the esterification process by reaction with the alkali compound and to remove the salts produced by the neutralization from the phosphate. To this end, the first step includes a first substep of washing the phosphate to be treated with an aqueous solution of an alkali compound; a second substep of removing the added aqueous solution from the phosphate; a third substep of rinsing the phosphate with water to remove therefrom the alkali compound yet remaining in the phosphate after the second substep; and a fourth substep of removing from the phosphate the water mixed therewith in the previous substep.

When the phosphate is washed with an aqueous solution of an alkali in the first step, the alkali reacts with the impurities produced in the esterification process so as to neutralize them. The salts produced are insoluble in the aqueous solution, which is then separated from the phosphate. A minor portion of the alkali compound may well remain in the phosphate and is therefore removed by rinsing with water. After the rinsing operation the water is removed from the phosphate.

The aqueous solution used in the first step preferably contains 1% to 7% by weight of an alkali compound. A concentration lower than that would reduce the washing ability of the solution and require a longer time for the operation, while a higher concentration would decompose the phosphate. The alkali compound can be sodium hydroxide, potassium hydroxide, ammonium hydroxide, etc.

For effective washing the phosphate and the aqueous solution must be thoroughly stirred and mixed up. The time the washing is to continue varies with the amount of the phosphate to be treated, the amount of the aqueous solution added, the capacity of the stirrer, etc. Usually washing for 30 to 120 minutes at room temperature is sufficient.

The amount of the aqueous solution to be added preferably is equivalent in % by weight to the amount of the phosphate to be treated. If the amount of the aqueous solution is less than is required, the washing ability it lowered, while if it is more than is required, the next substep of separating the aqueous solution from the phosphate requires a longer time.

The next second substep for separation of the added solution includes stopping the stirrer so as to keep the mixture of the phosphate and the aqueous solution stationary until the two components are separated so that the aqueous solution lies above the phosphate. If necessary, the separating step may be conducted under a vaccum condition of less than 20 mmHg or both under vacuum and at 60° C. to 100° C.

In the next third substep of rinsing the phosphate being treated, the rinsing water suitable for use can be city water, well water (or hard water) or ion-exchanged water.

The phosphate and the rinsing water are put in a stirrer, which is then operated to cause the alkali compound remaining in the phosphate to be dissolved in the rinsing water. The rinsing water is renewed every 10 to 30 minutes of stirring until the pH of the rinsing water becomes about 7.

In the next fourth substep of separating from the phosphate the rinsing water in which the alkali compound has been dissolved, the previously mentioned method of separation by keeping the liquid stationary, or separation under reduced pressure or vacuum, or separation both under vacuum and at elevated temperature, or separation by means of acid clay or activated clay may be employed. Two or more of these methods of separation may be employed simultaneously. Thus the first step has been completed.

The second step of diluting the phosphate with aromatic insulating oil is intended to reduce the viscosity of the phosphate so as to make the next adsorbing step easier than otherwise. Examples of the aromatic oil suitable for use as diluent are alkyl naphthalene (which will be referred to as AN) such as diisopropyl naphthalene (which will be referred to as DIPN), and monosiopropyl naphthalene (which will be referred to as HIPN), diaryl (which will be referred to as DAA), alkyl benzene (which will be referred to as AB) and alkyl diphenyl (which will be referred to as ADP). The compounds are used individually or in combination of two or more of them.

The amount of the aromatic insulating oil to be mixed with the phosphate preferably is less than 60% by weight. Addition of a greater amount will reduce the incombustibility of the phosphate since the aromatic insulating oils are combustible.

The next third adsorbing step using acid clay is intended to remove the impurities such as monoaryl phosphate, diaryl phosphate, water, etc. that have not been removed in the first step from the phosphate that has been diluted in the second step. Therefore, the third step includes a first substep of causing acid clay to adsorb the above-mentioned impurities and a second substep of separating the added acid clay from the phosphate. It is necessary that the treatment of the diluted phosphate with acid clay should be conducted in an atmosphere of dry gas in order to prevent deterioration of the phosphate and improve the adsorbing ability of the clay. Air or inert gas such as nitrogen, carbon dioxide, argon, helium having a relative humidity of lower than 40% is suitable for use as the above-mentioned dry gas.

Before acid clay is used as the adsorbent, it preferably is dried by heating it at 60° C. to 200° C. for 5 to 20 hours. This treatment helps remove impurities such as water having lower boiling points from the clay and make it more activated to have a higher adsorbing ability. This drying treatment is not essential for the method of this invention but may be conducted only if and when necessary.

Although the amount of acid clay to be added to the phosphate being treated depends on the characteristics that the phosphate has before purification and those which it is required to attain after purification, the amount usually is 3% to 10% by weight of the diluted phosphate. An amount not exceeding 3% by weight would result in insufficient adsorption while an amount exceeding 10% by weight would result in a longer time required to separate the added acid clay from the phosphate in the next substep.

Preferably, the temperature at which the adsorbing step is conducted is 60° C. to 150° C. and the time for the step, about 30 to 120 minutes. The lower limit of the temperature depends on the viscosity of the diluted phosphate while the upper limit thereof is determined within the range which does not cause thermal deterioration of the phosphate.

The period of time for which the step is conducted must be long enough to effect thorough mixing of the phosphate and the added acid clay. Since the time depends on the amount of the phosphate being treated and the performance of the stirrer, it may exceed the above-mentioned range of 30 to 120 minutes.

The acid clay that was mixed with the phosphate in the above substep is removed from the diluted phosphate in the next substep by means of a centrifugal separator or a filter press. Prior to putting the phosphate into the separator or press, it is kept stationary so that the acid clay settles down as a lower layer, with the phosphate forming an upper layer thereon.

The fourth step of removing impurities from the phosphate under reduced pressure is intended to finally remove water and other impurities still remaining in the liquid being treated by evaporating them. The reduced pressure or vacuum enables effective evaporation of the impurities having lower boiling points at low temperature.

In this step the diluted phosphate is stirred while being heated at 60° C. to 100° C. under a vacuum of 10 mmHg, preferably less than 0.1 mmHg. The time for the treatment depends on the ability of the stirring machine and generally is about 20 to 120 minutes.

Preferred embodiments of the invention will now be described below, wherein the triaryl phosphates used are tricresyl phosphate (TCP), trixylenyl phosphate (TXP), triethylphenyl phosphate (TEP) and triisopropylphenyl phosphate (TPP).

TABLE 1 shows the characteristics of the phosphates that have been purified by the above-mentioned method of the invention.

Method 1 has been conducted in the following manner. In the first step the same amount of 20% sodium hydroxide water solution as the amount of the phosphate to be treated is mixed with the phosphate, and the mixture is stirred for about one hour and then kept stationary for separation of the added aqueous solution. Then city water is added to rinse the phosphate until the pH of the water becomes nearly 7, whereupon the mixed liquid is kept stationary to remove therefrom almost all of the added water. Then the phosphate is further treated under a vacuum of 20 mmHg at 60° C.

In the second step the aromatic insulating oil or oils shown in TABLE 1 are added to the phosphate as a diluent.

In the third step 3% by weight of the acid clay on which no drying treatment has been performed is added to the diluted phosphate, and the mixture is stirred at 70° C. for about one hour in an atmosphere of nitrogen gas having a relative humidity of 40%. The mixture is then first kept stationary to separate the acid clay from the phosphate, which is then put in a centrifugal separator to separate the remaining clay.

In the fourth step the resulting liquid is treated under a vacuum of 10 mmHg at 60° C. for about 70 minutes while it is being stirred for further removal of the remaining impurities therefrom.

Method 2 has been conducted in the following manner. In the first step the same amount of 5% sodium hydroxide water solution as the amount of the phosphate to be treated is mixed with the phosphate, and the mixture is stirred for about 40 minutes, and then kept stationary for separation of the added water solution. Then ion-exchanged water is added to rinse the phosphate until the pH of the water becomes about 7, whereupon the mixture is kept stationary to separate therefrom almost all of the added ion-exchanged water. Then the phosphate is further treated under a vacuum condition of 5 mmHg at 80° C.

In the second step the aromatic insulating oil or oils as shown in TABLE 1 are added as a diluent to the phosphate.

In the third step 5% by weight of the acid clay that has been dried by heating it at 150° C. for 10 hours is added to the diluted phosphate, and the mixture is stirred at 90° C. for about 40 minutes in an atmosphere of dry nitrogen gas having a relative humidity of less than 5%. The mixture is then first kept stationary to separate the acid clay from the phosphate, and the remaining clay is removed by a filter press.

In the fourth step the diluted phosphate is treated under a vacuum condition of 0.1 mmHg at 60° C. for about 30 minutes while it is being stirred for further removal of the remaining impurities therefrom.

For comparison the electrical characteristics of a mixture (Control 1) of TCP and 50% by weight of DIPN and the characteristics of a mixture (Control 2) of the same components which has been treated by acid clay only are given in the lowest two columns of TABLE 1.

Table 1

| Triaryl phosphate | Method of Purifying | Diluent (% by weight) | tanδ (%) (at 80° C.) | ρ (Ωcm) (at 80° C.) | Breakdown Voltage (kV- 2.5 mm) |
|---|---|---|---|---|---|
| TCP | 1 | DIPN(40) | 0.8 | $1 \times 10^{13}$ | 55 |
| TCP | 1 | DIPN(30) MIPN(10) | 0.8 | $3 \times 10^{13}$ | 56 |
| TXP | 1 | DIPN(60) | 0.5 | $6 \times 10^{13}$ | 58 |
| TEP | 1 | DAA (40) | 0.7 | $1 \times 10^{13}$ | 55 |
| TEP | 1 | AB (50) | 0.7 | $9 \times 10^{12}$ | 58 |
| TPP | 1 | ADP (60) | 0.9 | $7 \times 10^{12}$ | 52 |
| TCP | 2 | DAA (40) | 0.7 | $1 \times 10^{13}$ | 54 |
| TEP | 2 | DAA (40) | 0.8 | $2 \times 10^{13}$ | 52 |
| TEP | 2 | DIPN(30) | 0.9 | $2 \times 10^{13}$ | 54 |
| TXP | 2 | ADP (50) | 0.9 | $9 \times 10^{12}$ | 52 |
| TPP | 2 | DIPN(20) MIPN(10) | 0.8 | $3 \times 10^{13}$ | 55 |
| TPP | 2 | AB (50) | 0.7 | $1 \times 10^{13}$ | 57 |
| TCP | Control 1 | DIPN(50) | 45 | $5 \times 10^{10}$ | 45 |
| TCP | Control 2 | DIPN(50) | 20 | $3 \times 10^{11}$ | 47 |

As can be seen from the above table, each of the phosphates has a dielectric loss tangent (tan δ) of 0.5% to 0.9% and a volume resistivity (ρ) of more than $7 \times 10^{12}$ Ωcm and a breakdown voltage of higher than 52 kV/2.5 mm.

These characteristics are obviously superior to those of Control 1 (tan δ of 45%, volume resistivity of $5 \times 10^{10}$ Ωcm and breakdown voltage of 45 kV/2.5 mm) and those of Control 2 (tan δ of 20%, volume resistivity of $3 \times 10^{11}$ Ωcm and breakdown voltage of 47 kV/2.5 mm).

The improved electrical characteristics of the phosphate that has been treated by the method of the invention enable the phosphate to serve as effective insulating oil, and yet the incombustibility of the phosphate is not affected or deteriorated at all.

The phosphates treated or purified by the method of the invention are particularly suitable for use as an impregnant oil of capacitors.

As described above, the purifying method of the invention enables effective and sufficient removal of impurities from the phosphates for improvement of the electrical characteristics thereof to such an extent as to make them suitable for use as insulating oil in electrical devices such as capacitors, without ever deteriorating the incombustibility of the oils.

What we claim is:

1. A method of purifying a triaryl phosphate to be used as electrical insulating oil, comprising: a first step of washing said phosphate, said first step including a first substep of washing said phosphate with an aqueous solution containing from approximately 1 percent to approximately 7 percent by weight of an alkali compound, a second substep of separating said solution from said phosphate, a third substep of rinsing said phosphate with water, and a fourth substep of separating said water from said phosphate; a second step of diluting said phosphate with an amount of an aromatic insulating oil effective to reduce the viscosity of said phosphate; a third step of treating said diluted phosphate with an adsorbent acid clay in an atmosphere of dry gas so that said clay adsorbs the impurities in said phosphate; and a fourth step of treating said phosphate under reduced pressure for removal of any remaining impurities therefrom.

2. The method of claim 1, wherein said alkali compound is sodium hydroxide.

3. The method of claim 1, wherein said first substep comprises washing said phosphate with an equivalent amount in % by weight of aqueous solution of said alkali compound.

4. The method of claim 1, wherein said third substep is continued until the pH of said water becomes about 7.

5. The method of claim 1, wherein said water is ion-exchanged water.

6. The method of claim 1, wherein said second and fourth substeps comprise keeping said phosphate stationary for separation of said aqueous solution and said water from said phosphate.

7. The method of claim 1, wherein said second and fourth substeps are conducted under a vacuum condition of less than 20 mmHg.

8. The method of claim 1, wherein said second and fourth substeps are conducted under reduced pressure and at an elevated temperature of 60° C. to 100° C.

9. The method of claim 1, wherein said aromatic insulating oil is alkyl naphthalene.

10. The method of claim 9, wherein said alkyl naphthalene is diisopropyl naphthalene.

11. The method of claim 9, wherein said alkyl naphthalene is monoisopropyl naphthalene.

12. The method of claim 9, wherein said alkyl naphthalene is a mixture of monoisopropyl naphthalene and diisopropyl naphthalene.

13. The method of claim 1, wherein 10% to 60% by weight of said aromatic insulating oil is added to said phosphate for dilution thereof in said second step.

14. The method of claim 1, wherein said third step comprises a first substep of mixing said phosphate with acid clay in an atmosphere of dry gas so that said acid clay adsorbs impurities in said phosphate and a second substep of separating said acid clay from said phosphate.

15. The method of claim 1, wherein said third step is conducted at 60° C. to 110° C.

16. The method of claim 1, wherein 3% to 10% by weight of said acid clay is added to said diluted phosphate in said third step.

17. The method of claim 1, wherein said acid clay used in said third step is previously dried at 60° C. to 200° C.

18. The method of claim 1, wherein said dry gas used in said third step is air having a relative humidity of less than 40%.

19. The method of claim 1, wherein said dry gas used in said third step is an inert gas.

20. The method of claim 19, wherein said inert gas is nitrogen.

21. The method of claim 19, wherein said inert gas is carbon dioxide.

22. The method of claim 14, wherein said second substep comprises keeping said mixture of said phosphate and said acid clay stationary for separation of the two components from each other.

23. The method of claim 14, wherein said second substep employs a filter press for separation of said acid clay from said phosphate.

24. The method of claim 1, wherein said fourth step is conducted under a vacuum of less than 10 mmHg.

25. The method of claim 1, wherein said fourth step is conducted at 60° C. to 100° C.

26. The method of claim 1, wherein said fourth step is conducted under a vacuum of less than 10 mmHg and at 60° C. to 100° C.

* * * * *